United States Patent [19]

Amini et al.

[11] Patent Number: 5,235,077
[45] Date of Patent: Aug. 10, 1993

[54] PROCESS FOR PREPARING PHENYL ESTERS OF SUBSTITUTED ACIDS

[75] Inventors: Bijan Amini, Moorestown, N.J.; Donald J. Dumas, Wilmington, Del.; Ronald A. Fong, Modesto, Calif.; George C. Sonnichsen, Wilmington, Del.

[73] Assignee: E. I. Du Pont de Nemours and Company, Wilmington, Del.

[21] Appl. No.: 674,498

[22] Filed: Mar. 25, 1991

[51] Int. Cl.$^5$ ............................................. C07C 51/00
[52] U.S. Cl. ................................... 554/152; 554/185
[58] Field of Search ............... 200/410.5; 554/152; 544/185

[56] References Cited

U.S. PATENT DOCUMENTS 2,073,937  3/1937  Kyrides .............................. 260/103
2,659,697  11/1953  Waco et al. ........................... 252/51

FOREIGN PATENT DOCUMENTS 267047  5/1988  European Pat. Off. .
0402047  12/1990  European Pat. Off. .
0444742  9/1991  European Pat. Off. .

Primary Examiner—José G. Dees
Assistant Examiner—Deborah D. Carr
Attorney, Agent, or Firm—Charles E. Krukiel

[57] ABSTRACT

An improved process for preparing phenyl esters of alkanoyloxyacetic acids in which phenyl chloroacetate is reacted with the salt of a carboxylic acid.

20 Claims, No Drawings

PROCESS FOR PREPARING PHENYL ESTERS OF SUBSTITUTED ACIDS

BACKGROUND OF THE INVENTION

The present invention relates to an improved process for preparing phenyl esters of the general formula (I):

$$R-\overset{O}{\underset{\|}{C}}-OCH_2-\overset{O}{\underset{\|}{C}}-OPh \qquad (I)$$

More particularly, the present invention relates to an improved process for preparing phenyl esters of alkanoyloxyacetic acids in which a salt of a carboxylic acid is reacted with phenyl chloroacetate (II):

$$ClCH_2-\overset{O}{\underset{\|}{C}}-OPh \qquad (II)$$

The subject phenyl esters of formula (I) are described in U.S. Pat. No. 4,778,618 and are useful as bleach activators. They are conventionally prepared from the corresponding acyloxyacetic acids using methods which are described in U.S. Pat. No. 4,778,618.

In U.S. Pat. No. 4,778,618, Fong et al. describe the following synthesis of alkyl esters of acyloxyacetic acids and references U.S. Pat. 2,659,697, U.S. Pat. No. 2,350,964 and *The Journal of the American Chemical Society*, 1952, Vol. 74, 3935–3936.

$$R-\overset{O}{\underset{\|}{C}}-O^-Na^+ + ClCH_2-\overset{O}{\underset{\|}{C}}-OH \xrightarrow{NaOAc}$$

$$R-\overset{O}{\underset{\|}{C}}-OCH_2-\overset{O}{\underset{\|}{C}}-OH \text{ (III) } \xrightarrow{Cl-\overset{O}{\underset{\|}{C}}-\overset{O}{\underset{\|}{C}}-Cl}$$

$$R-\overset{O}{\underset{\|}{C}}-OCH_2-\overset{O}{\underset{\|}{C}}-Cl \xrightarrow{R^*OH} R-\overset{O}{\underset{\|}{C}}-OCH_2-\overset{O}{\underset{\|}{C}}-OR^*$$

Other examples in U.S. Pat. No. 4,778,618 demonstrate that acyloxyacetic acids (III) may be synthesized by the following alternate route:

$$R-\overset{O}{\underset{\|}{C}}-Cl + HOCH_2-\overset{O}{\underset{\|}{C}}-OH \longrightarrow (III)$$

Thus, known processes requires three or more steps to prepare a phenyl ester of formula (I); they proceed via a substituted acetic acid and they require the preparation of at least one acid chloride.

U.S Pat. Nos. 3,984,454 and 4,154,953 disclose a method for preparing prostanoic acid esters of the formula $$PG-CH_2X-Y$$

wherein PG is the prostanoyloxy radical of a prostaglandin, X is a carbon-carbon single bond, carbonyl or carbonyloxy, and Y is substituted phenyl. By the disclosed method, the unesterfied prostaglandin is reacted, in the presence of an agent which splits off halogen halide, with a compound of the formula Hal—CH₂—X—Y wherein Hal is a halogen atom, preferably bromine, and X and Y have the values given above. Although starting prostaglandins are all characterized by possessing a esterfiable -COOH group, no other acids are disclosed as undergoing the reaction.

*Roczniki Chemii*, 1967, Vol 41, 1915–1920 describes the reaction of 4-nitrophenyl bromoacetate with N-protected amino acids to give depsipeptides of glycolic acid. This reaction was not reported with the less expensive and less reactive chloroacetate, with esters derived from phenols other than nitrophenol or with acids other than amino acids.

EP Patent 179,023 describes the reaction of phenyl bromoacetate with polyglutamic acid to give the corresponding phenyloxycarbonylmethyl esters.

GB Patent 1,209,631 describes the reaction of certain phenyl chloroacetates with 4-(1-pyrazolinyl)benzoates to give phenyl esters of benzoyloxyacetic acids. These compounds are claimed as fluorescent whitening agents. The reaction of 1-(4'-carboxyphenyl)-3-(4''-chlorophenyl)-2-pyrazoline with phenyl chloroacetate in the presence of triethylamine is specifically disclosed. The reaction of phenyl chloroacetate with carboxylic acids other than the subject 1-(4'-carboxyphenyl)-3-(substituted phenyl)-2-pyrazolines (i.e., fatty acids) is not reported.

U.S. Pat. No. 4,600,783 describes the reaction of salts of indometacin with tert-butyl chloroacetate in the presence of an inert organic solvent and a phase transfer catalyst. The use of phenyl chloroacetate (II) or of fatty acids in this process is not reported.

U.S. Pat. No. 4,985,180 describes the reaction of salts of 4-(chloroacetyloxy) benzenesulfonic acid and alkanoic acids to give alkanoyloxyacetyloxybenzenesulfonate salts.

SUMMARY OF THE INVENTION

The present invention is an improved process for preparing phenyl esters of the general formula (I)

$$R-\overset{O}{\underset{\|}{C}}-OCH_2-\overset{O}{\underset{\|}{C}}-OPh \qquad (I)$$

wherein R is linear or branched chain $C_5$–$C_{11}$ alkyl, which comprises treating phenyl chloroacetate in the optional presence of a solvent, with an alkali metal, alkaline earth metal or ammonium salt of a $C_6$–$C_{12}$ carboxylic acid, which may be preformed or generated in situ from a base and the carboxylic acid, in the optional presence of a phase transfer catalyst, and in the optional presence of a catalytic amount of a bromide or iodide salt. When the salt of the $C_6$–$C_{12}$ carboxylic acid is generated in situ from an alkali metal carbonate, bicarbonate or hydroxide or an alkaline earth metal carbonate or hydroxide, water is formed as a by-product which may be removed as it is formed by distillation from the reaction mixture.

DETAILED DESCRIPTION OF THE INVENTION

According to the present invention, it is now possible to prepare phenyl esters of the following formula (I) by a substantially improved and more economical process than currently known:

$$R-\overset{O}{\underset{\|}{C}}-OCH_2-\overset{O}{\underset{\|}{C}}-OPh \qquad (I)$$

wherein R is $C_5-C_{11}$ linear or branched chain alkyl.

According to the process of this invention, the phenyl esters of formula (I) are prepared as shown in Equations 1 and 2.

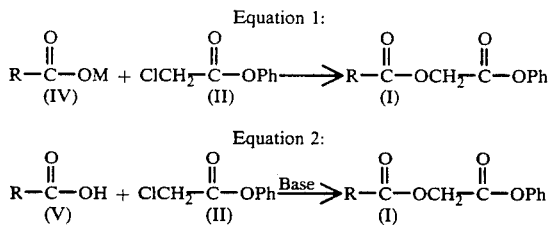

In this process, phenyl chloroacetate (II) is treated, in the optional presence of a solvent, with an alkali metal, alkaline earth metal or ammonium of a $C_6-C_{12}$ carboxylic acid, which may be preformed or generated in situ from a base and the carboxylic acid, in the optional presence of a phase transfer catalyst, and in the optional presence of a catalytic amount of a bromide or iodide salt to yield a phenyl ester of formula (I). When the salt of the $C_6-C$ carboxylic acid is generated in situ from an alkali metal carbonate, bicarbonate or hydroxide or an alkaline earth metal carbonate or hydroxide, water is formed as a by-product which may be removed as it is formed by distillation from the reaction mixture.

Phenyl chloroacetate (II) may be prepared by any convenient method, such as those described in Chemiche Berichte 1910, Vol. 43, 214, Hoppe-Seyler's Zeitschrift fuer Phisiologische Chemie, 1981, Vol. 362, 745-753, The Journal of Organic Chemistry 1959, Vol. 24, 1523-1526, and The Journal of Organic Chemistry, 1988, Vol. 53, 3321-3325, the teachings of which are incorporated herein by reference. A particularly useful process for the preparation of phenyl chloroacetate is described in U.S. application Ser. No. 07/674,401, having Attorney Docket No. CH-1781, filed concurrently herewith. Aliphatic carboxylic acids or formula (V) and their salts of formula (IV) may be prepared by methods which are well known in the art, although many are commercially available and may be purchased.

The process of Equations 1 and 2 is best carried out in an organic solvent, or mixtures of organic solvents, at temperatures between $-20°$ and $200°$ C. For reasons of convenience and economy, the process of Equations 1 and 2 is preferably carried out at a temperature of from 20° to 100° C. When lower boiling solvents are employed, higher rates of reaction may be obtained by conducting the reaction under pressure at temperatures above the atmospheric boiling point of the solvent.

Preferably, the reactoin is carried out in a solvent selected from aliphatic or aromatic hydrocarbons, halogenated aliphatic or aromatic hydrocarbons, cycloalkanes, dialkylamides, cyclic tertiary amides, ethers, cyclic ethers, polyethers, cyclic polyethers, alkylnitriles, dialkylketones, dialkylsulfoxides, secondary alcohols, tertiary alcohols and mixtures thereof. Typical solvents include dimethylsulfoxide, dimethylformamide, dimethylacetamide, 1-methyl-2-pyrrolidinone, acetonitrile, tetrahydrofuran, acetone, methyl ethyl ketone, methyl isobutyl ketone, toluene, xylenes, hexanes, heptanes and mixtures thereof It is also possible to carry out the reaction in the absence of a solvent. Polar aprotic solvents such as dimethylsulfoxide, dimethylformamide, dimethylacetamide, 1-methyl-2-pyrrolidinone, acetone, methyl ethyl ketone, methyl isobutyl ketone and acetonitrile are preferred with the amide solvents and acetonitrile being the most preferred solvents for use in the process.

The bases which may be employed in the process of this invention include, but are not limited to, alkali metal carbonates, alkali metal bicarbonates, alkali metal hydroxides, alkaline earth metal carbonates, alkaline earth metal hydroxides, relatively non-nucleophilic metal alkoxides, such as potassium tert-butoxide and relatively non-nucleophilic organic bases such as N,N-diisopropylethylamine, 2,2,6,6,-tetramethylpiperidine, 1,4-diazabicyclo[2.2.2]octane, 1,5-diazabicyclo[4.3.0]-non-5-ene and 1,8-diazabiocyclo[5.4.0]undec-7-ene. Sodium carbonate and potassium carbonate are preferred because of their lower cost and ease of use.

The term "alkali metals" as used herein refers to the Group 1a metals lithium, sodium, potassium, rubidium and cesium. The term "lkaline earth metals refers to the Group 2a metals beryllium, magnesium, calcium, strontium and barium.

In solvent systems in which the salt of the carboxylic acid is relatively insoluble, the process may be accelerated by the addition of a catalytic amount of an organic ammonium salt, phosphonium salt, amine, phosphine or polyether. Quaternary arsonium salts and N-alkylphosphoramides may also be beneficially employed as catalysts for this process, although concerns about their cost and/or toxicity would normally preclude their use. Quaternary ammonium salts, quaternary phosphonium salts and polyethers, such as those described by W. P. Weber and G. W. Gokel in "Phase Transfer Catalvsts in Organic Synthesis" (Springer-Verlag: W. Berlin, 1977), C. M. Starks and C. L. Liotta in "Phase Transfer Catalysis", Principles and Techniques" (Academic Press: N.Y., N.Y., 1978), and E. V. Dehmlow and S. S. Dehmlow in "Phase Transfer Catalysis" (Verlag Chemie: W. Berlin, 1980), the teachings of which are incorporated herein by reference, are particularly useful catalysts in the practice of this invention. Although any amount of catalyst may be employed, it is more practical to use between 0.1 and 10 mole percent relative to the phenyl chloroacetate (II) with 0.5 to 5 more percent being preferred.

Quaternary ammonium and quaternary phosphonium salt catalysts which may be used in practicing this invention include, but are not limited to, tetramethylammonium bromide, tetramethylammonium chloride, tetramethylammonium hydrogen sulfate, tetramethylammonium sulfate, tetramethylammonium iodide, tetraethylammonium bromide, tetraethylammonium chloride, tetraethylammonium hydrogen sulfate, tetraethylammonium iodide, tetrapropylammonium bromide, tetrapropylammonium chloride, tetrapropylammonium hydrogen sulfate, tetrapropylammonium iodide, methyltriethylammonium bromide, methyltriethylammonium chloride, methyltriethylammonium hydrogen sulfate, methyltriethylammonium iodide, methyltripropylammonium bromide, methyltripropylammonium chloride, methyltripropylammonium hydrogen suflate, methyltripropylammonium iodide, methyltributylammonium bromide, methyltributylammonium chloride, methyltributylammonium hydrogen sulfate, methyltributylammonium iodide, tetrabutylammonium fluoride, tetrabutylammonium dihydrogenphosphate, tetrabutylammonium bromide, tetrabutylammonium chloride, tetrabutylammonium hydrogen sulfate, tetrabutylammonium methanesulfonate, tetrabutylammonium paratoluene sulfonate, methyltrioctylammonium bromide, methyltrioctylammonium chloride, methyltrioctylammonium iodide, methyltridecylammonium chloride, octadecyltrimethylammonium bromide, Aliquat® 336-PTC, Arosurf® PT 40, Arosurf® PT 41, Arosurf® PT 50, Arosurf® PT 61, Arosurf® PT 62, Arosurf® PT 64, Arosurf® PT 71, Adogen® 464, hexadecyltrimethylammonium bromide, hexadecyltrimethylammonium chloride, hexadecyltrimethylammonium paratoluene sulfonate, hexadecyltributylammonium bromide, dimethylethylhexadecylammonium bromide, tetraoctylammonium bromide, tetradodecylammonium bromide, didecyldimethylammonium bromide, dimethyldistearylammonium methanesulfonate, myristyltrimethylammonium bromide, hexadecylpyridinium bromide, hexadecylpyridinium chloride, benzyltrimethylammonium bromide, benzyltrimethylammonium chloride, benzyltriethylammonium bromide, benzyltriethylammonium chloride, benzyltributylammonium bromide, benzyldimethylhexadecylammonium chloride, benzyldimethyldodecylammonium chloride, benzyltriphenylammonium chloride, (diisobutylphenoxyethoxyethyl)dimethylbenzylammonmium chloride, phenyltrimethylammonium bromide, phenyltrimethylammonium chloride, tetrabutylphsophonium bromide, tetrabutylphosphonium chloride, hexadecyltributylphosphonium bromide, dodecyltricyclohexylphosphonium bromide, tetraphenylphosphonium bromide, tetraphenylphosphonium chloride, methyltriphenylphosphonium bromide, methyltriphenylphosphonium iodide, N-alkyl-4-(N',N'-dialkylamino)pyridinium salts, such as those described by D. J. Brunelle and D. A. Singleton in *Tetrahedron Letters* 1984, Vol. 25, 3383-3386, the teachings of which are incorporated herein by reference, bis-aminopyridinium salts such as those described by D. J. Brunelle in U.S. Pat. No. 4,595,760, the teachings of whcih are incorporated herein by reference, N,N,N-trialkyl-2oxo-2-phenoxyethanaminium halides, which may be prepared by the method described by S. E. Drewes, H. E. M. Magojo and J. Gliemann in *Hoppe-Seyler's Zietschrift fuer Phisiologische Chemie* 1981, Vol. 362, 745-753, or modifications thereof, and (2-oxo-2-phenoxyethyl)triarylphosphonium halides, which may be prepared by the methods described by H. Kunz and H. Kauth in *Zeischrift fur Naturforschung* 1979, Vol. 34b, 1737-1744, or modifications thereof. Tetramethylamonium chloride has been found to be a particularly economical catalyst for this process.

Polyether catalysts which may be employed in practicing this invention include 12-crown-4, 15-crown-5, benzo-15-crown-5, 18-crown-6, dibenzo-18crown-6, dicyclohexano-18-crown-6, di dicyclohexano-24-crown-8, 5,6,14,15-dibenzo-1,4-8,12-diazacyclopentadeca-5,14-diene, 4,7,13,16,21,24-hexaoxa-1,10-diazabicyclo[8.8.8]hexacosane, 4,7,13,16,21-pentaoxa-1,10-diazabicyclo[8.8.5]tricosane, polyethylene glycol 400 dimethyl ether, polyethylene glycol 600 dimethyl ether, polyethylene glycol 1000 dimethyl ether, polyethylene glycol 2000 dimethyl ether, and tris[2-(2-methoxyethoxy)ethyl]amine.

The amines and amine salts which may be employed in the process of the invention include optionally substituted primary, secondary or tertiary aliphatic amines, optionally substituted primary, secondary or tertiary aromatic amines, pyridine, substituted pyridines and their salts. Preferred catalysts from this group include trialkyl amines and dialkylaminopyridines and their hydrogen halide salts. Examples of amines and amine salts which may be employed include, but are not limited to, trimethylamine, trimethylamine hydrochloride, triethylamine, triethylamine hydrochloride, triethylamine hydrofluoride, tripropylamine, tributylamine, pyridine, pyridine hydrobromide and 4-dimethylamino pyridine.

The phosphines which may be employed as catalysts in the process of the invention include trialkylphosphines and triaryphosphines, particularly tertiary phosphines such as triphenylphosphine, trimethylphosphine, triethylphosphine, tripropylphosphine and tributylphosphine.

The presence of a catalyst is particularly beneficial when solvents other than sulfoxides and amides are employed in carrying out the reaction. Thus, significant reaction rate enhancements can be obtained in solvents such as aliphatic or aromatic hydrocarbons, cycloalkanes, ethers, cyclic ethers, polyethers, cyclic polyethers, alkylnitriles and dialkylketones. Preferred solvents for use in conjunction with a phase transfer catalyst are toluene, xylenes, hexanes, heptanes, cyclohexane, tetrahydrofuran, dioxane, dimethoxyethane, acetone, methyl ethyl ketone, methyl isobutyl ketone and acetonitrile. Acetonitrile is a particularly useful solvent when used in conjunction with catalysts described above.

In the practice of this invention, the order of addition of reagents is not critical; however, since phenyl chloroacetate (II) can be degraded under basic conditions, addition sequences which minimize or eliminate exposure of the phenyl chloroacetate (II) to the base prior to addition of the carboxylic acid (IV) are preferred. Although not essential, it is often advantageous to carry out the reaction under an inert gas, such as nitrogen or argon. It will be recognized by those skilled in the art that the reaction mixtures generated in the practice of this invention will often be slurries and that in such cases efficient mixing is required for optimum results. It will be further recognized by those skilled in the art that when a relatively insoluble inorganic base is employed, it will often be advantageous to use this base in a high surface area form. In general, powdered forms of these bases are preferred.

The process of Equations 1 and 2 may be carried out using any practical ratio of phenyl chloroacetate (II) and the aliphatic carboxylic acid (V) or carboxylic acid salt (IV). In most cases, a 1:1 molar ratio of reactants is satisfactory, or between 0.95 and 1.10 molar equivalents of the carboxylic acid (V) or carboxylic acid salt (IV) may be used. In the practice of the process of Equation 2, any practical ratio of base to the aliphatic carboxylic acid (V) can be employed. In many cases, a 1:1 molar ratio of reagents is satisfactory; however, when a relatively insoluble inorganic base is employed, it is often convenient to use an excess of base.

While it is convenient in most cases to carry out the process of this invention in a manner that allows for the in situ generation of the carboxylic acid salt, those skilled in the art will recognize that the carboxylic acid salt may also be generated in a discreet reaction step and then combined with phenyl chloroacetate (II). When a pre-formed carboxylic salt (IV) is employed in the process of this invention, it is often beneficial to add between about 0.001 and 0.10 molar equivalents of a base such as those described above to neutralize any acids which might be introduced along with the phenyl chloroacetate (II).

It will be recognized by those skilled in the art that the use of certain bases such as metal carbonates, metal bicarbonates and metal hydroxides for the in situ generation of carboxylic acid salts will result in the generation of by-product water. It has been found that under certain conditions, the presence of by-product water results in a decreased yield of the ester of formula (I). While this effect is often small in dipolar, aprotic solvents such as dialkylamides, cyclic dialkylamides and dialkylsulfoxides, significant yield loses have been noted in other solvent systems. In such cases it is advantageous to carry out the reaction under conditions which allow for the continuous removal of the water by distillation from the reaction mixture. Depending upon the solvent and the pressure under which the reaction is carried out, the by-product water may be removed in a pure form, as a mixture with the solvent, or as an azeotrope.

The presence of iodide or bromide in the process of this invention can have a beneficial effect on both rate of the reaction and on the quality of the product obtained. The iodide or bromide may be introduced by employing: (1) an ammonium or phosphonium salt catalyst in which the counter ion is iodide or bromide; (2) an alkali metal iodide or bromide; or (3) an alkaline earth metal iodide or bromide. Examples of metal iodides include sodium iodide and potassium iodide. Examples of metal bromides include sodium bromide and potassium bromide.

Although any amount of iodide or bromide source may be employed, it is more practical to use between 0.1 and 10 mole percent relative to the phenyl chloroacetate (II) with 0.5 to 5 mole percent being preferred.

Phenyl esters of formula (I) can be isolated by filtration to remove insoluble solids followed by evaporation of any solvent employed. Alternatively, any solvent employed could be removed and the crude product then washed with water and dried in a conventional manner. In cases in which the solvent is immiscible with water, the reaction mixture may be washed with water prior to evaporation of the solvent. The esters of formula (I) may be further purified by further washing with water or by distillation.

EXAMPLE 1

Preparation of Nonanoyloxyacetic Acid,

Phenyl Ester, Using DMF as Solvent

To a slurry of 6.9 g of powdered potassium carbonate in 50 ml of dimethylformamide was added 4.4 ml of nonanoic acid followed by 4.25 g of distilled phenyl chloroacetate (prepared according to the procedure given in *The Journal of Organic Chemistry* 1959, Vol. 24, 1523-1526). The resulting mixture was stirred for 25 hours at 25.C and then poured over 250 ml of ice water and the product extracted with ethyl acetate (3×125 ml). The combined extracts were washed with water (3×200 ml), dried over magnesium sulfate, and stripped to give 6.22 g of yellow oil. The crude product was purified by flash column chromatography eluting with 10% ethyl acetate in hexane to give 4.6 g of colorless oil. NMR ($CD_2Cl_2$) 0.9 (t, 3H, $CH_3$), 1.3 (m, 10H), 1.65 (m, 2H), 2.45 (t, 2H), 5.83 (s,2H,$CO_2CH_2CO_2$), 7.1 (m, 2H), 7.25 (m, 1H), 7.4 (m,2H).

EXAMPLE 2

Preparation of Nonanoyloxyacetic Acid,

Phenyl Ester, in Acetonitrile Using

Tetramethylammonium Chloride as Catalyst

To a stirred flask containing 258 g of 99% crude phenyl chloroacetate (prepared by a modification of the procedure given in *The Journal of Organic Chemistry* 1959, Vol. 24, 1523-1526, in which an excess of chloroacetyl chloride was employed and the excess chloroacetyl chloride removed from the product by sparging with dry nitrogen), 2.7 l acetonitrile, 3.3 g of tetramethylammonium chloride and 159 g of powdered sodium carbonate was added 60 ml of a solution of 281 ml of 98% nonanoic acid in 300 ml of acetonitrile. The mixture was then heated to 75 C. over 70 minutes During this time a further 320 ml of the nonanoic acid solution was added dropwise. The remaining nonanoic acid solution was added during the first 20 minutes at 75° C. After the nonanoic acid addition was complete, the mixture was held at 75° C. for a additional 2.5 hours. The solvent was then removed under reduced pressure and the residue washed successively with 2.5 l and 1 l portions of water. The cloudy organic layer was dried over magnesium sulfate and filtered to give 329 g of amber oil.

The product was analyzed by gas chromatography using a HP-1 capillary column with FID detector and using the following temperature program: 5 min. at 100° C., following by a 20° C./min. temperature increase until the temperature reached 200° C., 6 min. at 200° C., followed by 25° C./min. temperature increase to 250° C., and finally a 10 min. hold at 250° C. The following components were noted (GC area %): 0.8% phenol, 2.6% 2-methyloctanoyloxyacetic acid, phenyl ester, 91.3% nonanoyloxyacetic acid, phenyl ester, and 3.5% nonanoyloxyacetoxyacetic acid, phenyl ester.

EXAMPLE 3

Preparation of Nananoyloxyacetic Acid, Phenyl Ester,
in Acetonitrile with Simultaneous Addition of Phenyl
Chloroacetate and Nonanoic Acid To a stirred flask containing 80.2 g of phenol and 1.85 g of tetramethylammonium chloride at 123° C., 102.3 g of chloroacetyl chloride was added over a period of 1 hour. After 2 additional hours at 123° C., the reaction temperature was increased to 130° C. and the reactor contents sparged with nitrogen for 40 minutes. The reaction mixture was then cooled to 70° C. and added to 212.2 g of acetonitrile and 124.9 g of nonanoic acid. This mixture was then added over 1 hour to a stirred slurry of 88.47 g of powdered sodium carbonate in 14.1 g of nonanoic acid and 377.1 g of acetonitrile at 80° C. After 2 additional hours, analysis of the reaction mixture by gas chromatography (FID detector) showed the major components (other than acetonitrile) in GC area % to be 2.9% phenol, 90.4% a mixture of nonanoyloxyacetic acid phenyl ester and 2-methyloctanoyloxyacetic acid, phenyl ester, and 3.0% nonanoyloxyacetoxyacetic acid, phenyl ester.

The acetonitrile was removed by distillation under reduced pressure. After cooling, 1042 g of water was added, the mixture was stirred, and the aqueous layer was then separated. Another 417 g of water was added, the pH adjusted to 5 with concentrated HCl, the mixture stirred, the layers separated, the organic layer dried with 40 g of magnesium sulfate which was removed by filtration to give 205.4 g of product. Analysis of the product by gas chromatography (FID detector) showed the major components in GC area % to be 1.0% phenol, 90.5% a mixture of nonanoyloxyacetic acid, phenyl ester, and 2-methyloctanoyloxyacetic acid, phenyl ester, and 4.4% nonanoyloxyacetoxyacetic acid, phenyl ester.

EXAMPLE 4

Preparation of Nonanoyloxyacetic Acid, Phenyl Ester, in Acetonitrile with Water Removal To a resin kettle equipped with a five-plate Oldershaw distillation column, a mechanical stirrer, a thermometer and an addition funnel was added 540.2 g of acetonitrile, 63.6 g of powdered sodium carbonate and 0.66 g tetramethylammonium chloride. The addition funnel was filled with acetonitrile. The mixture was heated to its boiling point, 83° C., and allowed to stir at this temperature until the distillation column became hot and acetonitrile began distilling overhead. The loss of condensate was measured, and acetonitrile was continuously added from the dropping funnel to maintain a constant volume in the reaction flask. A mixture of 102.4 g of phenyl chloroacetate, prepared by the procedure described in Example 3, 94.9 g of nonanoic acid and 47.0 g of acetonitrile was then added over a two-hour period. Following the addition, the mixture was kept at 83 C for an additional hour. Throughout the reaction period, the condensate was collected (a mixture of acetonitrile and water) and replaced continuously with dry acetonitrile from the addition funnel. Analysis of the reaction mixture by gas chromatography (FID detector), after 1 hour of the hold period, showed the starting phenyl chloroacetate to be completely converted and the major products by GC area % to be 1.1% phenol, 91.1% of a mixture of nonanoyloxyacetic acid, phenyl ester, and 2-methyl-octanoyloxyacetic acid, phenyl ester, and 4.3% non-anoyloxyacetoxyacetic acid, phenyl ester.

EXAMPLE 5

Preparation of Nonanoyloxyacetic Acid,

Phenyl Ester, in Acetonitrile Using 2 Mole%

Tetramethylammonium Chloride as Catalyst

A mixture of 17.0 g phenyl chloroacetate, prepared by the procedure in Example 2, 14.6 g nonanoic acid and 31.9 g acetonitrile was added over a ten minute period to a stirred flask containing 10.6 g powdered sodium carbonate, 0.23 g tetramethylammonium chloride, 2.0 g nonanoic acid and 124 g acetonitrile at 79° C. After 4 additional hours at 79° C., analysis of the reaction mixture by gas chromatography (FID detector) showed the starting phenyl chloroacetate to be completely reacted and the major products in GC area % to be 2.5% phenol, 87.6% a mixture of nonanoyloxyacetic acid, phenyl ester, and 2-methyloctanoyloxyacetic acid, phenyl ester, and 5.0% nonanoyloxyacetoxyacetic acid, phenyl ester.

EXAMPLE 6

Preparation of Nonanoyloxyacetic Acid, Phenyl Ester, in Acetonitrile Without a Catalyst A mixture of 10.2 g phenyl chloroacetate, prepared by the procedure in Example 2, 8.8 g nonanoic acid and 20.1 g acetonitrile was added over a 200 minute period to a stirred flask containing 6.4 g powdered sodium carbonate, 1.0 g nonanoic acid and 74.2 g acetonitrile at 79.C. After 17.5 additional hours at 79° C., analysis of the reaction mixture by gas chromatography (FID detector) showed in GC area %, 8.8% phenyl chloroacetate, 1.7% phenol, 80.4% a mixture of nonanoyloxyacetic acid, phenyl ester, and 2-methyloctanoyloxyacetic acid, phenyl ester, and 3.2% nonanoyloxyacetoxyacetic acid, phenyl ester.

EXAMPLE 7

Preparation of Nonanoyloxyacetic Acid, Phenyl Ester, in Acetonitrile Using 0.2 Mole% Tetramethylammonium Chloride as Catalyst A mixture of 10.2 g phenyl chloroacetate, prepared by the procedure in Example 2, 8.8 g nonanoic acid and 20.0 g acetonitrile was added over a 205 minute period to a stirred flask containing 6.4 g powdered sodium carbonate, 1.0 g nonanoic acid, 0.014 g tetramethylammonium chloride and 74.1 g acetonitrile at 78° C. After 17 additional hours at 79° C., analysis of the reaction mixture by gas chromatography (FID detector) showed in GC area %, 0.2% phenyl chloroacetate, 2.8% phenol, 87.4% a mixture of nonanoyloxyacetic acid, phenyl ester, and 2-methyloctanoyloxyacetic acid, phenyl ester, and 5.8% nonanoyloxyacetoxyacetic acid, phenyl ester.

EXAMPLE 8

Preparation of Nonanoyloxyacetic Acid, Phenyl Ester, in Acetonitrile at

Lower Temperature and Higher Concentration

A mixture of 34.1 g phenyl chloroacetate, prepared by the procedure in Example 3, 30.2 g nonanoic acid, 0.41 g tetramethylammonium chloride and 17.5 g acetonitrile was added over a 65 minute period to a stirred flask containing 21.1 g powdered sodium carbonate, 0.12 g tetramethylammonium chloride, 3.0 g nonanoic acid and 130.3 g acetonitrile at 56° C. After 9 additional hours at 56°-67° C., analysis of the reaction mixture by gas chromatography (FID detector) showed greater than 99% conversion of phenyl chloroacetate and the major products in GC area % to be 4.0% phenol, 84.7% a mixture of nonanoyloxyacetic acid, phenyl ester, and 2-methyloctanoyloxyacetic acid, phenyl ester, and 5.7% nonanoyloxyacetoxyacetic acid, phenyl ester.

EXAMPLE 9

Preparation of Nonanoyloxyacetic Acid,

Phenyl Ester, in Acetonitrile Using Tetrabutylammonium Chloride as Catalyst

A mixture of 10.2 g phenyl chloroacetate, prepared by the procedure in Example 2, 8.8 g nonanoic acid and 20.0 g acetonitrile was added over a 70 minute period to a stirred flask containing 6.4 g powdered sodium carbonate, 0.33 g tetrabutylammonium chloride, 1.0 g nonanoic acid and 74 g acetonitrile at 80° C. After 1 additional hour at 80° C., analysis of the reaction mixture by gas chromatography (FID detector) showed the starting phenyl chloroacetate to be completely reacted and products in GC area % of 1.3% phenol, 90.5% a mixture of nonanoyloxyacetic acid, phenyl ester, and 2-methyloctanoyloxyacetic acid, phenyl ester, and 3.9% nonanoyloxyacetoxyacetic acid, phenyl ester.

EXAMPLE 10

Preparation of Nonanoyloxyacetic Acid, Phenyl Ester, in Acetonitrile Using Tetrabutylphsophonium Chloride as Catalyst A mixture of 10.2 g phenyl chloroacetate, prepared by the procedure in Example 2, 8.8 g nonanoic acid and 20.1 g acetonitrile was added over a 60 minute period to a stirred flask containing 6.4 g powdered sodium carbonate, 0.34 g tetrabutylphosphonium chloride, 1.1 g nonanoic acid and 74.2 g acetonitrile at 80.C. After 3 additional hours at 80° C., analysis of the reaction mixture by gas chromatography (FID detector) showed the starting phenyl chloroacetate to be completely reacted and products in GC area % of 1.4% phenol, 92.4% a mixture of nonanoyloxyacetic acid, phenyl ester, and 2-methyloctanoyloxyacetic acid, phenyl ester, and 4.3% nonanoyloxyacetoxyacetic acid, phenyl ester.

EXAMPLE 11

Preparation of Nonanoyloxyacetic Acid, Phenyl Ester, in Toluene Using Tetramethylammonium Chloride as Catalyst A mixture of 17.1 g phenyl chloroacetate, prepared by the procedure in Example 2, 14.6 g nonanoic acid and 61 g toluene was added over a 25 minute period to a stirred flask containing 10.6 g powdered sodium carbonate, 0.26 g tetramethylammonium chloride, 2.1 g nonanoic acid and 215 g toluene at 100°-132° C. After 4 additional hours at 130°-116° C., analysis of the reaction mixture by gas chromatography (FID detector) showed the starting phenyl chloroacetate to be greater than 99% reacted and products in GC area % of 3.0% phenol, 75.1% a mixture of nonanoyloxyacetic acid, phenyl ester, and 2-methyloctanoyloxyacetic acid, phenyl ester, and 7.5% nonanoyloxyacetoxyacetic acid, phenyl ester.

EXAMPLE 12

Preparation of Nonanoyloxyacetic Acid, Phenyl Ester, in Acetonitrile Using Tetramethylammonium Chloride and Sodium Iodide as Catalysts A mixture of 17.0 g phenyl chloroacetate, prepared by the procedure in Example 3, 14.2 g nonanoic acid, 0.22 g tetramethylammonium chloride and 14.9 g acetonitrile was added over a 13 minute period to a stirred flask containing 10.6 g powdered sodium carbonate, 0.76 g sodium iodide, 2.4 g nonanoic acid and 61.8 g acetonitrile at 80° C. After 3.3 additional hours at 81° C., analysis of the reaction mixture by gas chromatography (FID detector) showed complete conversion of phenyl chloroacetate and products in GC area % of 1.4% phenol, 93.9% a mixture of nonanoyloxyacetic acid, phenyl ester, and 2-methyloctanoyloxyacetic acid, phenyl ester, and 2.4% nonanoyloxyacetoxyacetic acid, phenyl ester.

EXAMPLE 13

Preparation of Nonanoyloxyacetic Acid, Phenyl Ester, in Acetonitrile Using Tetramethylammonium Chloride and Sodium Bromide as Catalysts A mixture of 20.5 g phenyl chloroacetate, prepared by the procedure in Example 3, 16.8 g nonanoic acid, 0.28 g tetramethylammonium chloride and 5.4 g acetonitrile was added over a 1 hour period to a stirred flask containing 12.7 g powdered sodium carbonate, 0.64 g sodium bromide, 2.8 g nonanoic acid and 88.3 g acetonitrile at 80° C. After 2 additional hours at 78°-80° C., analysis of the reaction mixture by gas chromatography (FID detector) showed complete conversion of phenyl chloroacetate and products in GC area % of 1.2% phenol, 93.6% a mixture of nonanoyloxyacetic acid, phenyl ester, and 2-methyloctanoyloxyacetic acid, phenyl ester, and 3.7% nonanoyloxyacetoxyacetic acid, phenyl ester.

EXAMPLE 14

Preparation of Nonanoyloxyacetic Acid, Phenyl Ester, in Acetonitrile Using Anhydrous Sodium Nonanoate The sodium salt of nonanoic acid was prepared by adding 39.5 g of nonanoic acid in increments with mixing to 10 g of sodium hydroxide dissolved in 20 ml of water. The white solid was dried at 117° C. under vacuum and ground to a powder. To a flask was added 11.9 g of the sodium nonanoate, 10.2 g of phenyl chloroacetate, prepared by the procedure in Example 2, 0.13 g tetramethylammonium chloride and 94.0 g acetonitrile. The reaction mixture was heated to 80° C. with stirring. After 2 hours at 80° C., analysis of the reaction mixture by gas chromatography (FID detector) showed the starting phenyl chloroacetate to be completely reacted and products in GC area % of 0.5% phenol, 95.2% a mixture of nonanoyloxyacetic acid, phenyl ester, and 2-methyloctanoyloxyacetic acid, phenyl ester, and 2.4% nonanoyloxyacetoxyacetic acid, phenyl ester.

EXAMPLE 15

Preparation of Nonanoyloxyacetic Acid, Phenyl Ester, in Acetonitrile With Water Removal Prior to Phenyl Chloroacetate Addition A mixture of 9.8 g nonanoic acid and 15.5 g acetonitrile was added over a 60 minute period to a stirred flask containing 6.6 g powdered sodium carbonate, 0.07 g tetramethylammonium chloride and 94.1 g acetonitrile at 84.C. At the same time 150 ml of acetonitrile was added to the flask and 170 ml was removed by distillation. The reaction mixture was cooled to room temperature, 10.2 g of phenyl chloroacetate, prepared by the procedure in Example 3, and 0.23 g tetramethylammonium chloride was added and the mixture heated to 80° C. After 2 hours at 80° C., analysis of the reaction mixture by gas chromatography (FID detector) showed complete conversion of phenyl chloroacetate and products in GC area % of 1.2phenol, 92.1% a mixture of nonanoyloxyacetic acid, phenyl ester, and 2-methyloctanoyloxyacetic acid, phenyl ester, and 3.8% nonanoyloxyacetoxyacetic acid, phenyl ester.

EXAMPLE 16

Preparation of Nonanoyloxyacetic Acid, Phenyl Ester, in DMF at 88°-90°

A mixture of 17.0 g phenyl chloroacetate, prepared by the procedure in Example 2, 14.6 nonanoic acid and 23.5 g dimethylformamide was added over a 10 minute period to a stirred flask containing 10.6 g powdered sodium carbonate, 2.0 g nonanoic acid and 94.0 g dimethylformamide at 90 C. After 15 additional minutes at 88°-90° C., analysis of the reaction by gas chromatography (FID detector) showed complete conversion of phenyl chloroacetate and products in GC area % of 1.1% phenol, 89.3% a mixture of nonanoyloxyacetic acid, phenyl ester, and 2-methyloctanoyloxyacetic acid, phenyl ester, and 3.4% nonanoyloxyacetoxyacetic acid, phenyl ester.

EXAMPLE 17

Preparation of Nonanoyloxyacetic Acid, Phenyl Ester. in DMF at 55° C.

A mixture of 25.6 g phenyl chloroacetate, prepared by the procedure in Example 2, 22.4 g nonanoic acid and 31.0 g dimethylformaide was added over a 80 minute period to a stirred flask containing 8.8 g powdered sodium carbonate, 2.0 g nonanoic acid and 110.4 g dimethylformamide at 55° C. After 5 additional hours at 55° C., analysis of the reaction mixture by gas chromatography (FID detector) showed greater than 99% conversion of phenyl chloroacetate and products in GC area % of 1.4% phenol, 91.4% a mixture of nonanoyloxyacetic acid, phenyl ester, and 2-methyloctanoyloxyacetic acid, phenyl ester, and 2.9% nonanoyloxyacetoxyacetic acid, phenyl ester.

EXAMPLE 18

Preparation of Nonanoyloxyacetic Acid, Phenyl Ester, in DMF at 55° C. With Sodium Bromide as Catalyst A mixture of 20.5 g phenyl chloroacetate, prepared by the procedure in Example 2, 18.0 g nonanoic acid and 23.1 g dimethylformamide was added over a 80 minute period to a stirred flask containing 9.5 g powdered sodium carbonate, 1.5 g nonanoic acid, 0.62 g sodium bromide and 90.0 g dimethylformamide at 55° C. After 1 additional hour at 55° C., analysis of the reaction mixture of gas chromatography (FID detector) showed complete conversion of phenyl chloroacetate and products in GC area % of 0.4% phenol, 97.1% a mixture of nonanoyloxyacetic acid, phenyl ester, and 2-methyloctanoyloxyacetic acid, phenyl ester, and 1.3% nonanoyloxyacetoxyacetic acid, phenyl ester.

EXAMPLE 19

Preparation of Nonanoyloxyacetic Acid, Phenyl Ester, Using an Amine Base

To 33.2 g of nonanoic acid was added dropwise 27.2 g of diisopropylethylamine with stirring and ice bath cooling. The resulting solution was allowed to come to room temperature and then added dropwise with stirring to 34.2 g of distilled phenyl chloroacetate. The resulting mixture was then heated at 78°-86° C. for 2.5 hours and then allowed to cool to room temperature. The reaction mixture was partitioned between 50 ml of water and 50 ml of ethyl acetate, the layers separated and the organic layer washed with 5% hydrochloric acid (2×20 ml). The organic layer was dried over magnesium sulfate, filtered and the solvent removed under reduced pressure to give 57.9 g of amber oil. Analysis of the product by gas chromatography (FID detector) showed products in GC area % of 1.1% phenol, 1.0% phenyl chloroacetate, 88.2% a mixture of nonanoyloxyacetic acid, phenyl ester, and 2-methyloctanoyloxyacetic acid, phenyl ester, and 1.6% nonanoyloxyacetoxyacetic acid, phenyl ester.

EXAMPLE 20

Preparation of Nonanoyloxyacetic Acid, Phenyl Ester, in Acetone Using Tetramethylammonium Chloride and Sodium Bromide as Catalysts A mixture of 9.45 g sodium nonanoate, 8.7 g of phenyl chloroacetate, prepared by the procedure in Example 3, 0.52 g sodium bromide, 0.26 g of powdered sodium carbonate, and 100 ml of acetone was heated to 58° C. with stirring. After 6 hours at 58° C., the mixture was allowed to cool, filtered and the solvent removed under reduced pressure to leave 14.6 g of amber oil. Analysis of the product by gas chromatography (FID detector) showed products in GC area % of 1.2% phenol, 0.4% phenyl chloroacetate, 93.4% a mixture of nonanoyloxyacetic acid, phenyl ester, and 2-methyloctanoyloxyacetic acid, phenyl ester, and 2.6% nonanoyloxyacetoxyacetic acid, phenyl ester.

EXAMPLE 21

Preparation of Nonanoyloxyacetic Acid, Phenyl Ester in Methyl Ethyl Ketone Using Tetramethylammonium Chloride and Sodium Bromide as Catalysts A mixture of 9.45 g sodium nonanoate, 8.7 g of phenyl chloroacetate, prepared by the procedure in Example 3, 0.52 g sodium bromide, 0.26 g of powdered sodium carbonate, and 100 ml of methyl ethyl ketone was heated to 80°-82° C. with stirring. After 1 hour at 80°-82° C., the mixture was allowed to cool, filtered and the solvent removed under reduced pressure to leave 14.46 g of amber oil. Analysis of the product by gas chromatography (FID detector) showed complete conversion of phenyl chloroacetate and products in GC area % of 2.5% phenol, 87.6% a mixture of nonanoyloxyacetic acid, phenyl ester, and 2-methyloctanoyloxyacetic acid, phenyl ester, and 4.5% nonanoyloxyacetoxyacetic acid, phenyl ester.

EXAMPLE 22

Preparation of Nonanoyloxyacetic Acid, Phenyl Ester, in Acetonitrile Using 18-Crown-6 as Catalyst A mixture of 9.45 g sodium nonanoate, 8.52 g of distilled phenyl chloroacetate, 0.26 g of powdered sodium carbonate, 0.66 g of 18-crown-6, and 100 ml of acetonitrile was heated to 82.C. with stirring. After 1.5 hours at 82° C., the mixture was allowed to cool, filtered and the solvent removed under reduced pressure to leave 15.67 g of amber oil. The product was dissolved in 100 ml of ethyl acetate, washed with water (2×50 ml), dried over magnesium sulfate, and the solvent removed under reduced pressure to leave 14.76 g of amber oil. Analysis of the product by gas chromatography (FID detector) showed complete conversion of phenyl chloroacetate and products in GC area % of 0.8% phenol, 95.1% a mixture of nonanoyloxyacetic acid, phenyl ester, and 2-methyloctanoyloxyacetic acid, phenyl ester, and 1.8% nonanoyloxyacetoxyacetic acid, phenyl ester.

EXAMPLE 23

Preparation of a Mixture of Octanoyloxyacetic Acid, Phenyl Ester, and Decanovloxvacetic Acid, Phenyl Ester This material was prepared using the same procedure and scale as Example 4 except that 93.4 g of an acid mixture containing 59.3% octanoic acid and 40.7% decanoic acid was used in place of the 94.9 g of nonanoic acid. Analysis of the reaction mixture by gas chromatography (FID detector), after 1.5 hours of the hold period, showed products in GC area % of 0.6% phenyl chloroacetate, 2.0% phenol, 53.6% octanoyloxyacetic acid, phenyl ester, 33.4% decanoyloxyacetic acid, phenyl ester, 2.7% octanoyloxyacetoxyacetic acid, phenyl ester, and 1.6% decanoyloxyacetoxyacetic acid, phenyl ester.

EXAMPLE 24

Preparation of Nonanoyloxyacetic Acid, Phenyl Ester, in Acetonitrile Using TDA-1 as Catalyst A mixture of 9.45 g sodium nonanoate, 8.52 g of distilled phenyl chloroacetate, 0.26 g of powdered sodium carbonate, 0.85 g of TDA-1(tris[2-(2-methoxyethoxy)ethyl]amine), and 100 ml of acetonitrile was heated to 83° C. with stirring. After 4 hours at 83° C., the mixture was allowed to cool, filtered and the solvent removed under reduced pressure to leave 15.4 g of amber oil. The product was dissolved in 100 ml of ethyl acetate, washed with water (2×50 ml), dried over magnesium sulfate, and the solvent removed under reduced pressure to leave 14.26 g of amber oil. Analysis of the product by gas chromatography (FID detector) showed products in GC area % of 0.7% phenol, 0.3% phenyl chloroacetate, 95.4% a mixture of nonanoyloxyacetic acid, phenyl ester, and 2-methyloctanoyloxyacetic acid, phenyl ester, and 1.9% nonanoyloxyacetoxyacetic acid, phenyl ester.

EXAMPLE 25

Preparation of Nonanoyloxyacetic Acid, Phenyl Ester, in Acetonitrile Using Benzyltriethylammonium Chloride as Catalyst A mixture of 9.45 g sodium nonanoate, 8.52 g of distilled phenyl chloroacetate, 0.26 g of powdered sodium carbonate, 0.23 g of benzyltriethylammonium chloride, and 100 ml of acetonitrile was heated to 83° C. with stirring. After 1.5 hours at 83° C., the mixture was allowed to cool, filtered and the solvent removed under reduced pressure to leave 14.7 g of amber oil. Analysis of the product by gas chromatography (FID detector) showed complete conversion of phenyl chloroacetate and products in GC area % of 0.7% phenol, 95.3% a mixture of nonanoyloxyacetic acid, phenyl ester, and 2-methyloctanoyloxyacetic acid, phenyl es acetoxyacetic acid, phenyl ester.

EXAMPLE 26

Preparation of Nonanoyloxyacetic Acid, Phenyl Ester, in Acetone Using Benzyltriethylammonium Chloride as Catalyst A mixture of 9.45 g sodium nonanoate, 8.52 g of distilled phenyl chloroacetate, 0.26 g of powdered sodium carbonate, 0.23 g of benzyltriethylammonium chloride, and 100 ml of acetone was heated to 58° C. with stirring. After 3.0 hours at 58° C., the mixture was allowed to cool, filtered and the solvent removed under reduced pressure to leave 14.2 g of amber oil. Analysis of the product by gas chromatography (FID detector) showed products in GC area % of 1.4% phenol, 0.1% phenyl chloroacetate, 94.9% a mixture of nonanoyloxyacetic acid, phenyl ester, and 2-methyloctanoyloxyacetic acid, phenyl ester, and 1.9% nonanoyloxyacetoxyacetic acid, phenyl ester.

EXAMPLE 27

Preparation of Octanoyloxyacetic Acid, Phenyl Ester, in Acetonitrile Using N,N,N-Triethyl-2-oxo-2-phenoxyethanammonium Chloride as Catalyst A mixture of 8.82 g sodium octanoate, 8.52 g of distilled phenyl chloroacetate, 0.68 g of N,N,N-triethyl-2-oxo-2-phenoxyethanammonium chloride and 100 ml of acetonitrile was heated to 83° C. with stirring. After 1.5 hours at 83° C., the mixture was allowed to cool, filtered and the solvent removed under reduced pressure to leave 14.4 g of brown oil. Analysis of the product by gas chromatography (FID detector) showed products in GC area % of 3.1% phenol, 0.7% phenyl chloroacetate, 87.1% of octanoyloxyacetic acid, phenyl ester, and 1.9% octanoyloxyacetoxyacetic acid, phenyl ester.

EXAMPLE 28

Preparation of Octanoyloxyacetic Acid, Phenyl Ester, in Acetonitrile Using Triethylamine Hydrochloride as Catalyst A mixture of 8.82 g sodium octanoate, 8.52 g of distilled phenyl chloroacetate, 0.35 g of triethylamine hydrochloride and 100 ml of acetonitrile was heated to 83° C. with stirring. After 3.0 hours at 83° C., the mixture was allowed to cool, filtered and the solvent removed under reduced pressure to leave 14.2 g of amber oil. Analysis of the product by gas chromatography (FID detector) showed products in GC area % of 2.1% phenol, 0.7% phenyl chloroacetate, 87.8% of octanoyloxyacetic acid, phenyl ester, and 2.4% octanoyloxyacetoxyacetic acid, phenyl ester.

EXAMPLE 29

Preparation of Octanoyloxyacetic Acid, Phenyl Ester, in Acetonitrile Using Triethylamine as Catalyst A mixture of 8.82 g sodium octanoate, 8.52 g of distilled phenyl chloroacetate, 0.25 g of triethylamine and 100 ml of acetonitrile was heated to 83° C. with stirring. After 2.5 hours at 83° C., the mixture was allowed to cool, filtered and the solvent removed under reduced pressure to leave 14.7 g of brown oil. Analysis of the product by gas chromatography (FID detector) showed products in GC area % of 2.1% phenol, 0.7% phenyl chloroacetate, 90.4% of octanoyloxyacetic acid, phenyl ester, and 2.3% octanoyloxyacetoxyacetic acid, phenyl ester.

EXAMPLE 30

Preparation of Octanoyloxyacetic Acid, Phenyl Ester, in Acetonitrile Using (2-Oxo-2-phenoxyethyl)triphenylphosphonium Chloride as Catalyst A mixture of 8.82 g sodium octanoate, 8.52 g of distilled phenyl chloroacetate, 1.08 g of (2-oxo-2-phenoxyethyl)triphenylphosphonium chloride and 100 ml of acetonitrile was heated to 83° C. with stirring. After 1.5 hours at 83° C., the mixture was allowed to cool, filtered and the solvent removed under reduced pressure to leave 14.9 g of amber oil. Analysis of the product by gas chromatography (FID detector) showed complete conversion of phenyl chloroacetate and products in GC area % of 2.5% phenol, 88.8% of octanoyloxyacetic acid, phenyl ester, and 1.9% octanoyloxyacetoxyacetic acid, phenyl ester.

EXAMPLE 31

Preparation of Octanoyloxyacetic Acid, Phenyl Ester, in Acetonitrile

Using Triphenylphosphine as Catalyst

A mixture of 8.82 g of sodium octanoate, 8.52 g of distilled phenyl chloroacetate, 0.66 g of triphenylphosphine and 100 ml of acetonitrile was heated to 83° C. with stirring. After 1.5 hours at 83° C., the mixture was allowed to cool, filtered and the solvent removed under reduced pressure to leave 14.35 g of amber oil. Analysis of the product by gas chromatography (FID detector) showed complete conversion of phenyl chloroacetate and products in GC area % of 2.1% phenol, 87.2% of octanoyloxyacetic acid, phenyl ester, 3.5% triphenylphosphine, and 2.2% octanoyloxyacetoxyacetic acid, phenyl ester.

EXAMPLE 32

Preparation of 3,5,5-Trimethylhexanoyloxyacetic Acid, Phenyl Ester

This material was prepared using the same procedure as Example 4, except that 92.0 g of 3,5,5-trimethylhexanoic acid was used in place of nonanoic acid. Analysis of the reaction mixture by gas chromatography (FID detector), after a 70 minute hold period at 70° C., showed that the starting phenyl chloroacetate was completely converted and the major products by GC area % to be 3.5% phenol, 83.9% 3,5,5-trimethylhexanoyloxyacetic acid, phenyl ester, and 5.2% 3,5,5-trimethylhexanoyloxyacetic acid, phenyl ester.

We claim:

1. An improved process of preparing phenyl esters of the formula (I)

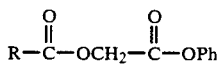
(I)

wherein R is linear or branched chain $C_5$–$C_{11}$ alkyl, which comprises treating phenyl chloroacetate in the optional presence of a solvent, with an alkali metal or alkaline earth metal salt of a $C_6$–C carboxylic acid in the optional presence of a catalytic amount of an organic ammonium salt, phosphonium slat, amine, phosphine or polyether, and in the optional presence of a catalytic amount of a bromide or iodide salt.

2. The process of claim 1 wherein the solvent is selected from dialkylamides, cyclic dialkylamides or dialkylsulfoxides.

3. The process of claim 2 wherein the salt of the carboxylic acid is a preformed sodium or potassium salt, the solvent is selected from the group consisting of dimethylsulfoxide, dimethylformamide, dimethylacetamide or 1-methyl-2-pyrrolidinone, and the process is conducted in the absence of a catalyst.

4. The process of claim 2 wherein the salt of the carboxylic acid is generated in situ from sodium carbonate, sodium bicarbonate, potassium carbonate or potassium bicarbonate, the solvent is selected from the group consisting of dimethylsulfoxide, dimethylformamide, dimethylacetamide or 1-methyl-2-pyrrolidinone, and the process is conducted in the absence of a catalyst.

5. The process of claim 2 wherein the salt of the carboxylic acid is preformed sodium or potassium salt, the solvent is selected from the group consisting of dimethylsulfoxide, dimethylformamide, dimethylacetamide or 1-methyl-2-pyrrolidinone, and the process is conducted in the presence of from 0.1 to 10 mole percent of a catalyst selected from sodium bromide, potassium bromide, sodium iodide and potassium iodide.

6. The process of claim 2 wherein the salt of the carboxylic acid is generated in situ from sodium carbonate, sodium bicarbonate, potassium carbonate or potassium bicarbonate, the solvent is selected from the group consisting of dimethylsulfoxide dimethylformamide, dimethylacetamide or 1-methyl-2-pyrrolidinone, and the process is conducted in the presence of from 0.1 to 10 mole percent of a catalyst selected from sodium bromide, potassium bromide, sodium iodide or potassium iodide.

7. The process of claim 1 wherein the solvent is selected from aliphatic or aromatic hydrocarbons, halogenated aliphatic or aromatic hydrocarbons, cycloalkanes, ethers, cyclic ethers, polyethers, cyclic polyethers, alkylnitriles or dialkylketones.

8. The process of claim 7 wherein the solvent is selected from toluene, xylenes, hexanes, heptanes, cyclohexane, tetrahydrofuran, dioxane, dimethoxyethane, acetone, methyl ethyl ketone, methyl isobutyl ketone or acetonitrile, and the process is conducted in the presence of from 0.1 to 10 mole percent of a quaternary ammonium or quaternary phosphonium salt as a catalyst.

9. The process of claim 8 wherein the salt of the carboxylic acid is a preformed sodium or potassium salt.

10. The process of claim 8 wherein the salt of the carboxylic acid is generated in situ from sodium carbonate, sodium bicarbonate, potassium carbonate or potassium bicarbonate.

11. The process of claim 10 wherein by-product water is removed as it is formed by distillation from the reaction mixture.

12. The process of claim 11 wherein the solvent is acetonitrile and the catalyst is tetramethylammonium chloride.

13. The process of claim 7 wherein the solvent is acetonitrile, tetrahydrofuran, acetone, methyl ethyl ketone, methyl isobutyl ketone, toluene, xylenes, hexanes or heptanes, and the process is conducted in the presence of from 0.1 to 10 mole percent of a quaternary ammonium or quaternary phosphonium chloride and from 0.1 to 10 mole percent of sodium bromide, potassium bromide, sodium iodide or potassium iodide as catalysts.

14. The process of claim 13 wherein the salt of the carboxylic acid is a preformed sodium or potassium salt.

15. The process of claim 13 wherein the salt of the carboxylic acid is generated in situ from sodium carbonate, sodium bicarbonate, potassium carbonate or potassium bicarbonate.

16. The process of claim 15 wherein by-product water is removed as it is formed by distillation from the reaction mixture.

17. An improved process of preparing phenyl esters of the formula

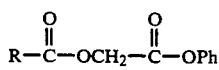
(I)

wherein R is linear or branched chain $C_5$–$C_{11}$ alkyl, which comprises treating phenyl chloroacetate in the optional presence of a solvent, with an ammonium salt of a $C_6$–$C_{12}$ carboxylic acid, and in the optional presence of a catalytic amount of a bromide or iodide salt.

18. The process of claim 17 wherein the solvent is selected from aliphatic or aromatic hydrocarbons halogenated aliphatic or aromatic hydrocarbons, cycloalkanes, ethers, cyclic ethers, polyethers, cyclic polyethers, alkylnitriles or dialkylketones.

19. The process of claim 17 wherein the solvent is selected from dialkylamides, cyclic dialkylamides or dialkysulfoxides.

20. An improved process of preparing phenyl esters of the formula

wherein R is linear or branched chain $C_5$–$C_{11}$ alkyl, which comprises treating phenyl chloroacetate in the presence of a solvent comprising acetonitrile with a sodium salt of a $C_6$–$C_{12}$ carboxylic acid in the presence of a catalytic amount of tetramethyl ammonium chloride, wherein said sodium salt is generated insitu from sodium carbonate and a $C_6$–$C_{12}$ carboxylic acid, and; said process further comprising removing water.

* * * * *